United States Patent [19]

Leacock

[11] 4,263,448

[45] Apr. 21, 1981

[54] PROCESS FOR OXIDATION OF HYDROCARBONS

[75] Inventor: James Leacock, New York, N.Y.

[73] Assignee: Halcon Research and Development Corp., New York, N.Y.

[21] Appl. No.: 25,505

[22] Filed: Mar. 30, 1979

[51] Int. Cl.³ .............................................. C07C 67/05
[52] U.S. Cl. .............................. 560/246; 260/348.32; 260/348.33; 260/545 R; 560/241; 562/412; 562/531; 562/536; 562/545; 568/476; 568/478; 568/557; 568/571; 568/577; 568/836; 568/837
[58] Field of Search .......................................... 560/246

[56] References Cited

U.S. PATENT DOCUMENTS

| 3,584,033 | 6/1965 | Copelin | 560/243 |
|---|---|---|---|
| 3,692,823 | 9/1972 | Gordon | 560/243 |
| 4,189,600 | 2/1980 | Weitz | 560/246 |

*Primary Examiner*—Natalie Trousof
*Assistant Examiner*—Michael Shippen
*Attorney, Agent, or Firm*—William C. Long; David Dick; Jack B. Murray, Jr.

[57] ABSTRACT

An oxidizable hydrocarbon is oxidized in a reaction zone at elevated temperature in the presence of a liquid reaction medium by introducing the hydrocarbon and a feed stream containing molecular oxygen to the reaction zone under conditions sufficient to oxidize at least a portion of the hydrocarbon; withdrawing at least a portion of the liquid reaction medium from the reaction zone; passing at least a portion of the withdrawn liquid reaction medium to an oxygen injection zone located external to the reaction zone; contacting the liquid in said oxygen-injection zone with a gas stream containing molecular oxygen under conditions sufficient to form a two-phase gas/liquid mixture; and passing said two-phase gas/liquid mixture to the reaction zone as the feed of molecular oxygen thereto.

5 Claims, 1 Drawing Figure

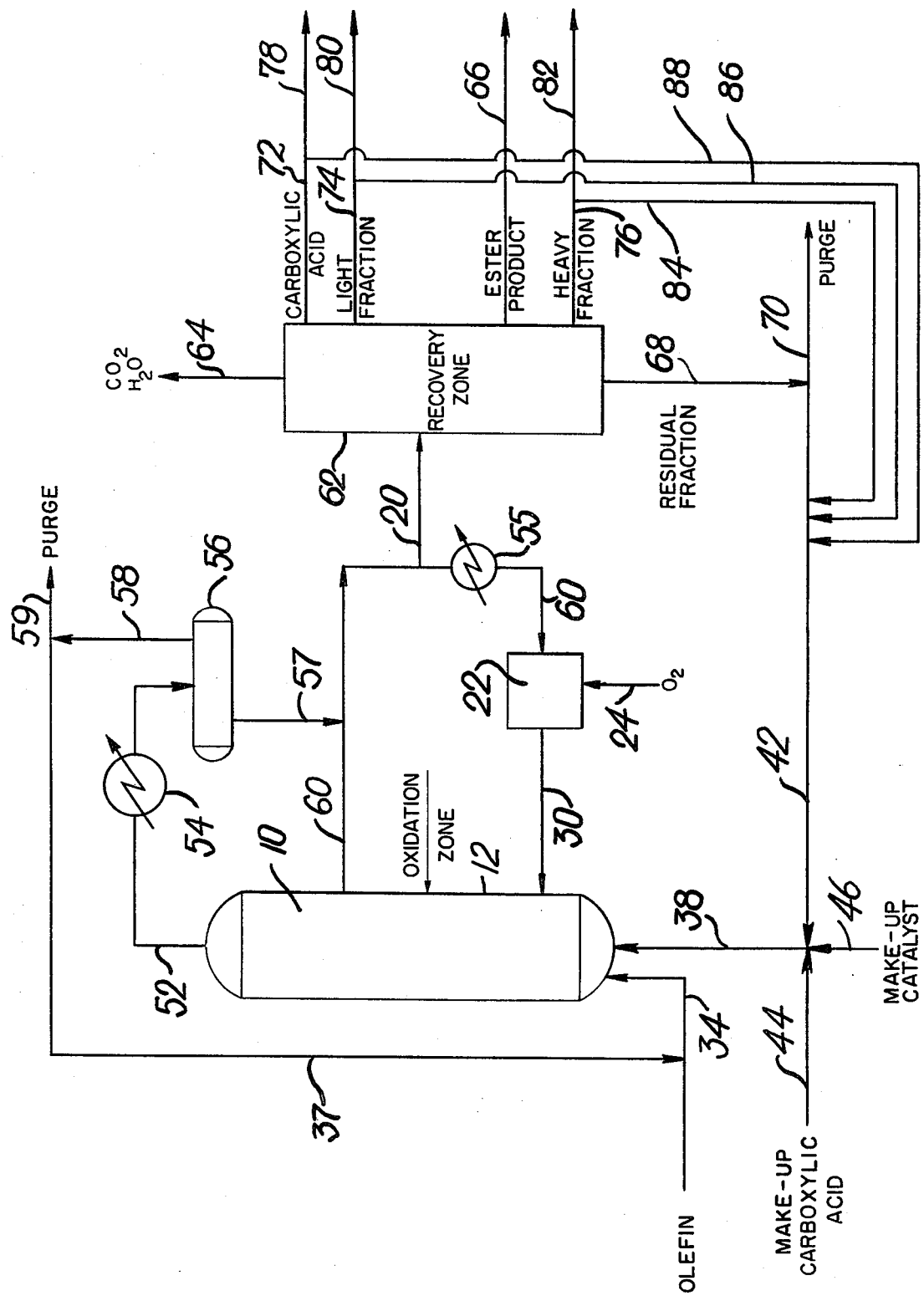

PROCESS FOR OXIDATION OF HYDROCARBONS

BACKGROUND OF THE INVENTION

1. Field of the Invention

This invention relates to the oxidation of hydrocarbons and is more particularly concerned with hydrocarbon oxidation employing an improved oxygen-injection method.

2. Description of the Prior Art

Glycol esters, and especially glycol carboxylic acid esters, are particularly useful organic chemical intermediates and extractive solvents. The glycol esters produced from ethylene are useful in the production of ethylene glycol an important commercial chemical. Catalytic processes for the preparation of the glycol esters have been disclosed, for example, in U.S. Pat. No. 3,689,535 and in Belgian Pat. No. 738,463. Ethylene glycol may be prepared by the hydrolysis of the ethylene glycol carboxylic acid esters, as disclosed in U.S. pat. No. 3,647,892, and vinyl acetate may be prepared by pyrolysis of the ethylene glycol ester, as disclosed in U.S. Pat. No. 3,689,535. Similarly, propylene glycol may be prepared by the hydrolysis of propylene glycol carboxylic acid esters, and other glycol esters yield the corresponding glycols upon suitable hydrolysis. (Belgian Pat. No. 862,054 (issued 1978) relates to an improved process for preparing glycol esters in which olefin, molecular oxygen, and a carboxylic acid are contacted in the presence of a catalyst system comprising a variable valent cation in association with bromine, chlorine, a bromine-containing compound or a chlorine-containing compound in a vertically-elongated reaction zone provided with a branch vertical circulation zone for continuously transferring liquid from the upper portion of the vertical reaction zone to the bottom of the reaction zone, to provide predetermined vertical superficial liquid velocities, which disclosure is herein incorporated by reference.

While the known processes for oxidizing hydrocarbons, such as those disclosed in the above-mentioned patents and patent applications, are effective for the indicated purposes, they are susceptible to improvement from the standpoint of optimum operation with continuous oxygen feeds to the reactor, generally by use of gas spargers. However, such devices which sparge gas into a liquid phase reaction medium containing the hydrocarbon reactants are quite vulnerable to loss of oxygen flow caused, for example, by a discontinuity in the feed pressure of the oxygen gas to the system. In such a case, the danger exists of back flow of part of the liquid reaction medium into the gas sparger. In start-up of the reactor following this discontinuity of oxygen feed, the spargers must be flushed to insure that the flammable hydrocarbons are removed from the spargers prior to passage of oxygen gas therethrough for safety's sake. This results in added equipment and process time expenses. In the event the flammable hydrocarbons are flushed using an inert gas, such as nitrogen, the large volumes of gas employed must be removed from the reactor's effluent gases and offer a potential environmental pollution source which must be carefully treated before discharging to the atmosphere. Use of a nonflammable flushing liquid which is inert to the components in the reactor can introduce impurities to the system, and, again, the volumes of flushing liquid can be expensive to recover from the reactor's product streams. The dilution of the reaction media resulting from use of such flushing liquids can also adversely affect reactor efficiency during startup, decreasing product yields, selectivity and quality. To avoid introduction of impurities in the system, the non-flammable liquid which would ordinarily be used to flush the spargers would be one which would be indigenous to the process. However, such liquids are themselves not entirely satisfactory. For example, in the case of the preparation of vicinal glycol esters by the above-described olefin-oxidation process, the only non-flammable liquid indigenous to the process is water, and it has been found that significant quantities of water, when passed through the gas spargers to flush them free of the hydrocarbon reactants, results in the deposit on the gas spargers and other process equipment of a resin-like material which is believed to result from the reaction of water with components of the liquid medium. Since this deposited resin-like material can readily plug the spargers and is organic in nature, the flushing of the gas spargers with water is unacceptable.

SUMMARY OF THE INVENTION

In accordance with the process of this invention, an oxidizable hydrocarbon is oxidized by means of molecular oxygen in a reaction zone at elevated temperature in the presence of a liquid reaction medium by:

(a) introducing said hydrocarbon and a feed stream containing molecular oxygen to said reaction zone under conditions sufficient to oxidize at least a portion of said hydrocarbon;

(b) withdrawing at least a portion of the liquid reaction medium from the reaction zone;

(c) passing at least a portion of the withdrawn liquid reaction medium to an oxygen-injection zone external to the reaction zone;

(d) contacting the liquid in said oxygen-injection zone with a gas stream containing molecular oxygen under conditions sufficient to form a two-phase gas/liquid mixture; and (e) passing said two-phase gas/liquid mixture to said reaction zone as the feed of molecular oxygen thereto.

The novel process of this invention provides a safe and highly efficient means of regulating the amount of oxygen introduced to the oxidation zone since the process of this invention permits the requisite gas valve controls to be located much closer to the point at which the oxygen is contacted with a liquid medium. This close association of valve controls and point of gas/liquid mixing is often not possible in the conventional practice of introducing the oxygen gas directly into the liquid reaction medium due to the bulk of the necessary valve controls and to the crowding in the near vicinity of the reactor of other various controls, piping, support structures and the like, as well as the thickness of the reactor walls, which are often heavily insulated for heat conservation.

Moreover, this invention avoids the need for use of inert fluids to flush oxygen gas injection ports in the reactor since the present invention, upon a decision to terminate the oxidation (as for example during shutdown of the reactor), permits the immediate cessation of oxygen injection while permitting the continued passage of the recycle liquid stream, without the oxygen, through the conduit connecting the external oxygen-injection station with the reaction zone, thereby preventing the fouling problems and avoiding the liquid back-up dangers which have been inherent in operation of conventional processes, as discussed above. Any desired flushing of oxygen injection ports in the external oxygen injection zone (e.g., with gaseous $N_2$) can be performed easily, with close control of gas flows therethrough.

DETAILED DESCRIPTION OF THE INVENTION

The improvement of this invention can be employed in connection with the liquid phase oxidation of a wide variety of oxidizable hydrocarbons. Illustrative of such hydrocarbon oxidation processes is the liquid phase oxidation of olefins to prepare vicinal glycol esters, as will be more fully discussed below. Other suitable liquid phase hydrocarbon oxidation processes and illustrative references to such processes, include (1) the oxidation of olefins with oxygen to form aldehydes, e.g., the oxidation of ethylene to form acetaldehyde (U.S. Pat. No. 3,076,032); (2) the oxidation of aldehydes with $O_2$ to prepare acids, e.g., the oxidation of acetaldehyde to form acetic acid and acetic anhydride (U.S. Pat. Nos. 2,254,725; 2,552,175; 3,119,862; 3,258,483); (3) the oxidation of cumene with $O_2$ to form cumene hydroperoxide (U.S. Pat. Nos. 2,613,227; and 2,619,510; (4) the oxidation of butane with $O_2$ to form acetic acid (U.S. Pat. No. 3,293,292); (5) the epoxidation of propylene with $O_2$ to form propylene oxide (U.S. Pat. No. 2,780,635); (6) the oxidation of cyclohexane with $O_2$ to form cyclohexanol (U.S. Pat. No. 3,239,552); (7) the epoxidation of ethylene with $O_2$ to form ethylene oxide (U.S. Pat. No. 2,985,668); (8) the $O_2$ oxidation of aldehydes to form percarboxylic acids, e.g., the preparation of peracetic acid from acetaldehyde (U.S. Pat. No. 3,228,977); (9) the $O_2$ oxidation of xylene to phthalic acids (U.S. Pat. No. 3,130,015); (10) the $O_2$ oxidation of ethylene in the presence of acetic acid to vinyl acetate (U.S. Pat. Nos. 3,253,020; 3,277,158); (11) the $O_2$ oxidation of propylene to form acrylic acid (U.S. Pat. No. 3,271,447); (12) the $O_2$ oxidation of p-menthane (i.e., p-methyl isopropyl cyclohexane) to form p-menthane hydroperoxide (U.S. Pat. No. 3,259,661); (13) the $O_2$ oxidation of isobutane to t-butyl hydroperoxide (Canadian Pat. No. 865,159); (14) the $O_2$ oxidation of ethyl benzene to ethyl benzene hydroperoxide (U.S. Pat. No. 3,475,498); and the like.

As will be apparent from the foregoing, the term "hydrocarbons" as used herein is intended to include cyclic and acyclic organic compounds such as alkanes, alkenes, cycloalkanes, cycloalkenes, and the like and aromatic organic compounds such as compounds containing one or more phenyl groups. The term also includes carbonyl (e.g., ketonic, aldehydic, carboxyl and the like) derivatives of the foregoing, as well as heterocyclic compounds.

Also, the terms "oxidation" and "oxidize", as used herein to describe the board aspect of this invention in treatment of the aforementioned hydrocarbons, are intended to refer to any reaction in which one or more carbon atom in an organic molecule is substituted by one or more oxygen groups (e.g., one or more of these groups: =O, —O— and —O—O—). These terms are therefore inclusive of reactions in which the product comprises at least one member selected from the group consisting of epoxides, aldehydes, carboxylic acids, hydroperoxides, percarboxylic acids, carboxylic acid esters and alcohols.

In such liquid phase hydrocarbon oxidations a reactor is charged, preferably continuously, with the selected oxidizable hydrocarbon and, optionally, a solvent for the hydrocarbon, together with catalyst and co-reactants, if necessary. The reactor can be heated to the desired temperature by conventional means, such as by use of a suitable reboiler. Generally, however, such oxidation processes are exothermic. If desired, one or more side-streams or product streams which are recycled to the reactor can be cooled, as by use of a suitable heat exchanger, for the purpose of removing heat of reaction. To this end, the present invention conveniently provides a method for controlling heat of reaction by providing a suitable cooler in the conduit which contains the portion of the liquid reaction medium withdrawn from the reactor which is intended to be passed to the external oxygen injection zone. The oxidizable hydrocarbon, solvent, catalyst and other components of the liquid phase reaction medium can be charged at any point in the reactor, but preferably are charged below the point in the reactor at which the two-phase gas/liquid mixture containing the oxygen feed thereto is introduced in accordance with the practice of this invention. The reactor, if desired, can also be provided with any suitable means for removing vapors as an overhead product and suitable cooling means, if desired, for condensing at least a portion of these withdrawn vapors to form condensate, e.g., for reflux to the reactor, if desired.

In accordance with the improvement provided by this invention, at least a portion of the liquid phase reaction medium is withdrawn from the oxidation zone and is passed to an oxygen-injection zone external to the oxidation zone in which the liquid is contacted with the selected gas stream containing molecular oxygen under conditions sufficient to form a two-phase gas/liquid mixture, which is then passed to the oxidation zone as the feed of molecular oxygen thereto.

The components of the liquid reaction medium in the oxidation reactor are not critical and in addition to the oxidizable hydrocarbon other components which are possible include inert solvents, diluents, extractants and the like. In addition, the reaction may be effected in the presence or in the absence of a suitable catalyst for the oxidation. Where present, the catalyst can be in the form of homogeneous or heterogeneous catalysts.

The process of this invention can be practiced in a batchwise, continuous or semi-continuous manner, with continuous practice being preferred. The proportion of the liquid-phase reaction medium which is withdrawn from the reactor for passage to the external oxygen injection zone can vary widely depending on such factors as the velocity of liquid required to maintain two-phase bubbly flow after injection of the oxygen, the particular hydrocarbon being oxidized and the like.

Generally, however, the liquid reaction medium will be withdrawn for passage to the oxygen injection zone in an amount of less than about 10% of the total mass of the liquid reaction medium in the reactor per minute, more typically less than about 5% of the total mass of the liquid reaction medium per minute.

The molecular oxygen-containing gas introduced to the liquid medium in the external oxygen-injection zone in accordance with the process of this invention can comprise molecular oxygen or any oxygen-containing gas such as air which does not contain gas components which would react with the reactants in the oxidation zone and thereby interfere with the desired oxidation. The molecular oxygen-containing gas is preferably supplied in concentrated form, i.e., having an oxygen content of 85 mol percent or more.

The temperature at which the molecular oxygen containing gas is contacted with the above-described portion of the withdrawn liquid reaction medium to form the two-phase mixture is not critical. Rather, these conditions will vary widely depending on the particular molecular oxygen-containing gas employed, the particular liquid being treated, the gas-injection apparatus, the relative dimensions of the liquid conduits entering and exiting the oxygen injection zone and other factors. Generally, the liquid temperature can vary from the freezing point to the bubble point at the selected pressure, and will, for example, generally range from about 50° to 200° C., more preferably from about 75° to 180° C., for treatment of liquid mixtures in recycle to oxidation zone for olefin-oxidation reactions in forming vicinal glycol esters. Similarly, the gas pressure will generally fall within the range of about 50 to 1,000 psig, more preferably from about 200 to 600 psig for liquids involved in olefin-oxidation reactions. However, higher pressures can easily be used where the apparatus is designed to withstand such higher pressures.

The flow rates of liquid and gas necessary to obtain and maintain the desired two-phase gas liquid mixture for a given gas and liquid at given conditions of temperature and pressure in a particular apparatus can be easily ascertained, achieved and controlled employing conventional means known to those skilled in the art. Thus, in continuous operations, the superficial liquid velocity of liquid passed from the oxygen injection zone to the reaction zone will generally fall within the range of about 3 to 100 feet per second, more preferably from about 5 to 60 feet per second, and most preferably from about 10 to 40 feet per second, for conduit diameters within the range of from about 1 to 12 inches.

The term "two-phase gas/liquid mixture" as used herein is intended to refer to gas/liquid mixtures which contain gas bubbles distributed throughout the liquid; the average diameter of the gas bubbles will generally be less than about 0.5 in., preferably less than about 0.25 in., and most preferably less than about 0.125 in. Such two-phase mixtures can, of course, also contain dissolved oxygen or other components of the gases so injected. However, the mass of such dissolved gases will be generally less than about 20% of the mass of gases present in the form of bubbles in the two-phase mixture. The gas bubbles in the two-phase mixture can, and generally will, vary in population across the vertical cross-section of the conduit through which the mixture is passed. Typically, a majority of the bubbles will, due to their buoyancy, be concentrated in the upper part of the conduit. However, the mixture should be substantially free of any bubbles or gas slugs having an effective bubble diameter greater than 8 times the average diameter of the gas bubbles in the mixture.

As used herein, the term "average bubble diameter" is intended to mean the Sauter mean bubble diameter, i.e., that diameter which represents the surface to volume ratio of the entire gas bubble population in a given volume of the gas/liquid mixture. See Perry's Chemical Engineering Handbook, p. 18-78 (5th ed. 1973). The gas surface and gas volume in the given gas/liquid mixture unit volume can be readily determined using conventional techniques, e.g., by observing the size distribution of gas bubbles in the mixture and calculating the total volume and surface area of the entire bubble population. The term "effective bubble diameter" as used herein is intended to mean the diameter of a hypothetical spherical gas bubble having the volume of the particular bubble or gas slug in question, and thus is a term which converts non-uniform or irregular bubbles to spherical measurement terms.

The precise means employed in the oxygen-injection station to effect the desired degree of mixing of the oxygen-containing gas with the liquid stream forms no part of this invention and can vary widely. Moreover, conventional gas-liquid mixing techniques, such as injecting the gas into the liquid by use of a plurality of gas injection nozzles, are well understood and their description is not necessary to a full understanding of this invention.

The conduit passing the two-phase gas/liquid mixture to the oxidation zone should be constructed in such a way to maintain the desired two-phase bubbly flow. The two-phase gas/liquid mixture, formed by this invention, can be passed to the oxidation zone by means of one or more conduits. Such conduits sould be free of branching along their length between the external oxygen injection zone and the oxidation reactor. Thus, if two or more conduits are employed, each should be provided in the external oxygen-injection zone with a separate oxygen-gas injection means so that the resulting two-phase gas/liquid mixture is not passed through any conduit having branching to, for example, divide one stream into two. Each conduit preferably has a substantially smooth inner surface and is therefore preferably substantially free of obstructions including joints, valves, measuring probes and the like, which are large enough to disrupt the flow pattern of the two-phase gas/liquid mixture such as to allow the undesired large bubbles or gas slugs to form either upstream or downstream of such obstructions.

Gradual decreasing of the conduit transverse cross-sectional areas, resulting for example, from the coupling of a larger diameter pipe to a pipe of small diameter, need not be entirely avoided, so long as two-phase gas/liquid flow is maintained. However, the transverse cross-sectional area is preferably not increased, since such increases will generally greatly increase the flow rates needed to maintain the desired two-phase gas/liquid mixture.

The conduit is also preferably substantially horizontal along its length from the external oxygen-injection zone to the oxidation reactor. Most preferably, any incline in the conduit is upwardly from the external oxygen-injection zone so that during upset conditions, as for example during shut-down of the oxidation reactor, any oxygen bubbles in the conduit will tend to flow forward to the reactor, rather than backwardly into the external oxygen-injection zone.

The conduit is also preferably substantially straight, i.e., substantially free of bends, in either the vertical or horizontal plane to avoid the segregation of the gas bubbles and formation of the undesired large bubbles or gas slugs due to the tendency of the more dense liquid phase to be forced to the outside portion of a curved conduit section.

The conduit can suitably employ in-line mixers positioned within the conduit carrying the two-phase gas/liquid mixture to assist in maintaining the desired two-phase bubbly flow by suitable mixing of the phases. Such in-line mixers generally have no moving parts and act to contort fluid flow in such a way as to impart the desired degree of mixing to the fluid. Suitable in-line motionless mixers include those manufactured by Kenics Corporation under their trandemark "Static Mixer" and those marketed by Komax Systems, Inc.

The length of the conduit, which is used to pass the two-phase gas/liquid mixture to the reactor according to this invention, is not critical. Generally, conduits having a length of 5 to 100 feet are entirely satisfactory. Of course, conduits of greater or lesser length can be used where desired.

The average residence time of the two-phase gas/liquid mixture in the conduit communicating the external oxygen injection zone with the reaction zone, is not critical and will vary, of course, depending on the conduit length, fluid flow rate and other factors. Generally, however, the average residence time will be less than about 20 seconds, and preferably less than about 10 seconds.

The two-phase gas/liquid mixture so formed is passed to the oxidation reactor and introduced thereto to provide the oxygen feed to the reactor. Of course, oxygen can be introduced to the reactor in minor amounts as a component either of the other liquid streams or of gaseous streams introduced to the oxidation zone. Generally, however, the oxygen contained in such other liquid streams will be less than about 10% of the moles of total oxygen introduced to the oxidation reactor by means of the two-phase gas/liquid mixture in accordance with the process of this invention.

Preferably, the two-phase gas/liquid mixture containing the oxygen is introduced to the reaction zone so as to uniformly distribute the oxygen feed across the width of the reactor, such as by use of a conventional injection distributing injection means. The point in the reactor at which this mixed stream is fed is not critical, although for most efficient operation the gas/liquid mixture will generally be introduced to the lower portion of the reaction zone.

Generally, the pressure in the conduit employed to introduce the two-phase gas/liquid mixture to the reactor will, at the point of introduction of this mixture into the reactor, be from about 1 to 50 psia, and preferably from about 5 to 30 psia, greater than the pressure in the liquid reaction medium within the reactor at the level in the reactor at which the two-phase mixture is introduced.

The point in the reactor at which the two-phase gas/liquid mixture is introduced in accordance with this invention will generally be below the point in the reactor at which the withdrawal of the liquid reaction medium is taken for supplying liquid to the external oxygen injection zone. However, this is not critical, and the liquid reaction medium can be withdrawn from the reactor at a point in the reactor below the injection of the two-phase gas/liquid mixture.

The product of the oxidation reaction can be withdrawn from the oxidation zone either as a vapor overhead product, as a condensate of a portion of the vapor overhead, as a separate side-stream from the liquid reaction medium or as a liquid phase bottoms product. Alternatively, a portion of the liquid phase reaction medium which is withdrawn according to this invention for passage to the external oxygen injection zone can, prior to this external oxygen injection zone, be removed via a second conduit for subsequent treatment to recover the desired product of the oxidation reaction.

The reaction system with which this invention is especially concerned relates to the production of monobasic carboxylic esters of vicinal glycols by the oxidation with molecular oxygen of an olefin in the presence of a monobasic carboxylic acid, and in the presence of a catalyst system comprising a non-noble metal variable valent cation plus at least one of bromine, chlorine, a bromine-containing compound or a chlorine-containing compound. Such catalyst systems are disclosed, for example, in U.S. Pat. No. 2,689,535, U.S. Pat. No. 3,668,239, British Pat. No. 1,289,535, and said patents are incorporated herein by reference.

The liquid-phase reaction medium with which this invention is particularly concerned and which is present in the oxidation zone contains the carboxylic acid, the glycol ester products of the reaction, precursors of the desired glycol ester products of the reaction, reaction by-products, including water and halogenated reaction by-products, as well as the catalyst system employed, dissolved olefin and dissolved oxygen also being present. Normally, the liquid reaction medium will contain from 5 to 60 mol percent of the carboxylic acid, and 5 to 60 mol percent of the reaction products including glycol dicarboxylate, glycol monocarboxylate, precursors of the desired esters and by-products. Such precursors include the glycol corresponding to the olefin itself, higher-boiling materials, ether alcohols, as well as halogenated precursors, the halogen being introduced into the system as a catalyst component. For example, when the olefin is ethylene, the carboxylic acid is acetic acid, and bromine or a bromine-containing compound is employed, such higher-boiling materials include diethylene glycol, tri-ethylene glycol and their mono- and di-acetate derivatives, and the halogenated precursors include ethylene bromohydrin, 2-bromoethyl acetate, 1,2-dibromoethane and brominated derivates of the higher-boiling materials. The principal by-product is water. The catalyst system will generally be present in the amount of 0.1 percent to 30 percent by weight. If desired, the reaction can be carried out in the presence of an inert solvent. Examples of such inert solvents are aromatic hydrocarbons, alkanols and esters, e.g., benzene, t-butanol, ethylene glycol diacetates, and the like. Preferably, however, the carboxylic acid reactant necessarily present in the liquid-phase reaction medium is used not only as the source of the acid moiety of the desired ester, but as a solvent as well. The reaction is carried out with continuous withdrawal from the oxidation zone of a stream which is processed to recover reaction products, unconverted reactants, and by-products, some of which are recycled to the oxidation zone as will be hereinafter discussed. At the same time, olefin and carboxylic acid, together with recycle components are continuously introduced into the reaction zone. The liquid feed can also suitably contain the catalyst components dissolved or suspended in it.

The invention will be more readily understood by reference to the accompanying drawing.

In the following discussion, the reactants are ethylene, acetic acid and oxygen, and the catalyst system is assumed to be cationic tellurium and anionic bromine, the latter being conveniently supplied as hydrogen bromide dissolved in acetic acid. Continuous operation is assumed. Referring to the drawing, an olefin, e.g., ethylene, is introduced through line 34, suitably by means of a conventional distribution device, e.g., a sparger (not shown), into oxidation zone 12 in which is maintained a body of liquid-phase reaction medium 10. The olefin is contacted in oxidation zone 10 with carboxylic acid, e.g., acetic acid, and catalyst, e.g., tellurium bromide, which are introduced to oxidation zone via conduit 38, and molecular oxygen which is introduced via stream 30. The recycle vapor stream in line 37 is mixed with the olefin stream in line 34. Such pre-mixing of the recycle vapor with the olefin feed is not required and the recycle vapor can also be introduced to oxidation zone 10 separately.

Vapor comprising unreacted ethylene and oxygen together with gaseous by products and diluents and more volatile components from the liquid phase reaction medium is withdrawn from oxidation zone 10 via conduit 52 and partially condensed in cooler 54. Condensed liquid and uncondensed vapor are separated from each other in separator 56. As shown, the condensed liquid is withdrawn through line 57 which feeds into line 60. Heat of reaction can, if desired, be removed by various means including coils (not shown). The uncondensed vapor is withdrawn from separator 56 through line 58 and a small quantity of this vapor can be purged via line 59 in conventional manner. The balance of the vapor is the recycled vapor stream returned to oxidation zone 10 via line 37.

A portion of the liquid phase reaction medium is continuously withdrawn from the oxidation zone via conduit 60. A portion of the withdrawn liquid phase reaction medium is passed from conduit 60 to line 20 for introduction to recovery zone 62. The balance of withdrawn liquid phase reaction medium is passed to an oxygen injection zone 22 located externally to reactor 12 in which the liquid is contacted with a gas stream containing molecular oxygen, introduced to zone 22 via line 24, to provide a two-phase gas/liquid mixture as above defined. This two-phase mixture is withdrawn from zone 22 via line 30 and passed as the oxygen feed to reactor 12. The liquid withdrawn via conduit 60 from reactor 12 can be optionally cooled, by means of cooler 55 prior to oxygen injection zone 22, e.g., to remove excess heat of reaction.

Recovery zone 62 is depicted schematically, but it normally comprises a series of distillation columns of conventional type and design, and which form no part of the present invention. Other low and high-boiling by-products are also recovered within recovery zone 62 and may be used as such or recycled as desired. Within recovery zone 62 are separated the desired diester product (ethylene glycol diacetate), low-boiling by-products and high-boiling by-products, which include components of the catalyst system. Within recovery zone 62 by-product water and carbon dioxide are also removed as separate components or conjointly, e.g., through line 64. The carbon dioxide by-product can, if desired, be returned to the oxidation system to facilitate control of the recycled vapor composition. This would normally require additional facilities (e.g., compression equipment, not shown). Alternatively, of course, carbon dioxide by-product can be discarded. The diester product is withdrawn from recovery zone 62, e.g., through line 66, and can be used as such, for example, as a solvent or plasticizer, or can be subjected to further processing such as, for example, hydrolysis to yield ethylene glycol or pyrolysis to yield vinyl acetate, for example, as described in Kollar U.S. Pat. No. 3,689,535.

The non-vaporized portion of the reaction mixture, which includes non-volatile catalyst components and by-products and co-products of higher molecular weight is shown as being withdrawn through line 68 as a residual fraction which forms part of the recycle stream being returned to the oxidation zone through line 42. Purging of this residual fraction can be effected through line 70 as required in accordance with conventional practice. Thus, as shown in the drawing, the separation of the reaction product mixture is suitably carried out to provide a carboxylic acid fraction which is removed through line 72, a light fraction of components having boiling points above that of acetic acid but below those of components of the ester product, and a heavy fraction of materials having higher boiling points than the product esters but more readily vaporizable than the components of the residual fraction. The light fraction is suitably withdrawn through line 74 and the heavy fraction through line 76. Portions of each of these streams can be withdrawn from the system as shown in the drawing via lines 78, 80 and 82 and the remaining portion, or the entire amount removed from the recovery zone, can be combined with the recycle stream in line 42 for return to the oxidation zone 10, as desired, lines 84, 86 and 88 being provided for this purpose. In any case, the recycle stream in line 42 is combined with the required amounts of make-up acetic acid and make-up catalyst and introduced into zone 10 through line 38.

The oxidation zone itself can be configured in any convenient form. For example, the reactor can comprise a stirred pressure vessel, a reactor tower (operated either in an upflow or downward flow mode), a packed bed reactor, a fluidized bed reactor and the like. In operation of such an olefin-oxidation process to form glycinol glycol esters, the reactor preferably comprises a vertical column which is provided with liquid downcomer means such as are described in Belgian Pat. No. 862,054 which has been referred to above. In such reactors, the vertically-elongated reaction zone is adapted to contain a body of liquid reaction mixture and is provided with a branch vertical circulation zone for continuously transferring liquid from the upper portion of the body of the liquid reaction mixture to the lower portion of that liquid body. Such vertical circulation, especially when combined with reactant introduction into the lower portion of the liquid reaction mixture under continuous conditions, provides a means for carefully controlling the selected superficial liquid velocity through the reaction zone and for varying the partial pressure profile of molecular oxygen through the reaction zone, each of which are important in order to insure a more uniform reaction zone temperature and to allow for effective suspension of particulate matter present in the reaction zone, thereby resulting in improved conversions, selectivities and yields of the desired vicinal glycol esters.

The following example will serve to illustrate this invention further but are not intended to limit the scope thereof. Unless otherwise indicated, all parts and percents are on a molar basis.

EXAMPLES

To a 750 gallon cylindrical reactor (45 feet in diameter × 60 feet in height), which is provided with a 1-inch diameter draw-off conduit arranged to maintain a 650 gallon liquid volume within the reactor, is charged the selected oxidizable hydrocarbon (where liquid at room temperature) and the selected solvent for the oxidizable hydrocarbon to fill the reactor to the designated liquid level. The reactor is then heated under nitrogen to the desired reaction temperature by means of an internal heating/cooling coil and liquid is continuously withdrawn from the reactor at a rate of about 30 gal./min., via the draw-off conduit and passed to a surge vessel located external to the reactor, from which the liquid is withdrawn, also at a rate of about 30 gal./min., via a 1-inch diameter horizontal conduit and recycled to the lower portion of the reactor. The conduit which communicates the surge vessel with the reactor has a length of 15 feet, is substantially free of bends, and has a substantially smooth inner surface. When the desired temperature is attained, a feed stream comprising the oxidizable hydrocarbon is introduced to the reactor below the liquid recycle point and molecular oxygen (175 psig, 150° C.) is injected at a gas flow rate of about 0.3 pounds per minute into the liquid about 5 feet downstream of the surge vessel by means of a 0.0156 inch diameter injection nozzle centrally positioned in the conduit to form a two-phase gas/liquid mixture, which is passed to the reactor at a superficial liquid velocity of 12 feet per second as feed of oxygen thereto.

The average residence time in the conduit communicating the external oxygen injection zone and the reactor is found to be about 0.75 seconds. The bubble population in the two-phase mixture thus formed is determined to have an average bubble diameter along the length of this conduit about 0.0125 inch, with the maximum observed bubble diameter being about 0.25 inch. The pressure in the conduit containing the two-phase gas/liquid mixture at the point of introduction of this mixture into the reactor is found to be about 25 psi greater than the pressure in the liquid reaction medium within the reactor at the level in the reactor at which the two-phase mixture is introduced.

Reactor pressure is maintained at the desired level by regulating the rate of gas withdrawal from the reactor. A portion of the liquid reaction medium is withdrawn from the reactor as a product stream via a separate conduit to provide a rate of product withdrawal equivalent to the feed rate of the oxidizable hydrocarbon. The process is continued for 16 hours, and the product formed by the oxidation is found to be present in each run in the withdrawn product stream.

The foregoing procedure is employed to oxidize the oxidizable hydrocarbons indicated in the Table below, wherein the composition of the liquid phase reaction medium, the product of oxidation and reaction conditions are also indicated for each run.

| Example No. | Oxidizable Hydrocarbon | Initial Reactor Charge | (wt. %) | Temperature (°C.) | Pressure (psig) | Product |
|---|---|---|---|---|---|---|
| 1 | propylene | benzene | 91.7 | 200 | 700 | propylene oxide |
|  |  | manganese propionate | 0.1 |  |  |  |
|  |  | nitrobenzene | 8.2 |  |  |  |
| 2 | ethylene | dibutyl phthalate | 77.0 | 220 | atm. | ethylene oxide |
|  |  | silver oxide (suspensoidal mixture) | 23.0 |  |  |  |
| 3 | ethylene | water[1] | 90.0 | 75 | atm. | acetaldehyde |
|  |  | $PdCl_2$ | 0.1 |  |  |  |
|  |  | $CuCl_2$ | 9.0 |  |  |  |
|  |  | $K^+$ salt of 1,2-naphtho-quinone-4-sulfonic sulfonic acid | 0.9 |  |  |  |
| 4 | cumene | cumene | 99.0 | 110 | atm. | cumene hydroperoxide |
|  |  | $CaCO_3$ | 1.0 |  |  |  |
| 5 | cumene | cumene | 100 | 130 | atm. | cumene hydroperoxide |
| 6 | ethyl benzene | ethyl benzene | 100 | 150 | 150 | ethyl benzene hydroperoxide |
| 7 | cyclohexane | cyclohexane | 92.6 | 165 | 125 | borate ester of cyclohexanol |
|  |  | benzene | 0.001 |  |  |  |
|  |  | metaboric acid | 7.4 |  |  |  |
| 8 | isobutane | t-butyl hydroperoxide | 25 | 125 | 370 | t-butyl hydroperoxide |
|  |  | t-butyl alcohol | 24 |  |  | t-butyl alcohol |
|  |  | isobutane | 51 |  |  |  |
| 9 | ethylene | glacial acetic acid | 91.0 | 145 | 400 | ethylene glycol acetic acid esters |
|  |  | $TeO_2$ | 0.8 |  |  |  |
|  |  | HBr | 8.2 |  |  |  |

[1] Water in overhead vapors returned to reactor as reflux.

It will be obvious that various changes and modifications can be made without departing from the invention, and it is intended, therefore, that all matter contained in the foregoing description shall be interpreted as illustrative only and not as limitative of the invention.

I claim:

1. In a process for forming vicinal glycol ester wherein an olefin is oxidized with molecular oxygen in a reaction zone at elevated temperature in the presence of a liquid reaction medium containing a monobasic carboxylic acid and catalyst for the reaction, the improvement which comprises:
   (a) withdrawing at least a portion of the liquid reaction medium containing vicinal glycol ester from the reaction zone;
   (b) passing at least a portion of the withdrawn liquid reaction medium to an oxygen-injection zone external to the reaction zone;
   (c) contacting the liquid in said oxygen-injection zone with a gas stream containing molecular oxygen under conditions sufficient to form a two-phase gas/liquid mixture containing gas bubbles having an average diameter of less than about 0.5 inch distributed throughout the liquid and containing dissolved gases in an amount of less than about 20% of the mass of gases present as said gas bubbles, said two-phase gas/liquid mixture being substantially free of gas bubbles having an effective bubble diameter greater than 8 times said average bubble diameter; and (d) passing said two-phase gas/liquid to said reaction zone as the feed of molecular oxygen thereto.

2. The process according to claim 1 wherein the two-phase gas/liquid mixture is characterized by a pressure of from about 50 to 1000 psig and a temperature of from about 50° to 200° C.

3. The process according to claim 1 wherein the two-phase gas/liquid mixture is passed to said reaction zone at a superficial liquid velocity of from about 3 to 100 feet per second through a conduit having a substantially smooth inner surface and being substantially free of bends, said conduit having a diameter within the range of from about 1 to 12 inches.

4. The process according to claim 3 wherein the average residence time of the two-phase gas/liquid mixture in said conduit is less than about 20 seconds.

5. The process according to claim 4 wherein the two-phase gas/liquid mixture comprises a liquid phase having gas bubbles distributed therein, said gas bubbles having an average diameter of less than about 0.25 inch.

* * * * *